United States Patent
Stanke et al.

(10) Patent No.: US 7,177,019 B2
(45) Date of Patent: *Feb. 13, 2007

(54) APPARATUS FOR IMAGING METROLOGY

(75) Inventors: Fred E. Stanke, Cupertino, CA (US);
Douglas E. Ruth, Sunnyvale, CA (US);
James M. Cahill, San Jose, CA (US);
Michael Weber, Sunnyvale, CA (US);
Clinton B. Carlisle, Palo Alto, CA
(US); Hung Pham, San Jose, CA (US);
Edric Tong, Sunnyvale, CA (US);
Elliot Burke, Santa Barbara, CA (US)

(73) Assignee: Tokyo Electron Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/048,552

(22) Filed: Feb. 1, 2005

(65) Prior Publication Data
US 2005/0128490 A1    Jun. 16, 2005

Related U.S. Application Data

(63) Continuation of application No. 09/533,613, filed on Mar. 22, 2000, now Pat. No. 7,042,580.

(60) Provisional application No. 60/125,462, filed on Mar. 22, 1999, provisional application No. 60/118,217, filed on Feb. 1, 1999.

(51) Int. Cl.
*G01B 11/24* (2006.01)

(52) U.S. Cl. .................. 356/237.2; 356/601; 356/630

(58) Field of Classification Search .. 356/237.1–237.5, 356/601–602, 609, 612, 614, 630–632, 445–448; 250/559.22, 559.27
See application file for complete search history.

(56) References Cited

U.S. PATENT DOCUMENTS 4,328,553 A * 5/1982 Fredriksen et al. .... 356/139.04

(Continued)

FOREIGN PATENT DOCUMENTS

EP    0 881 484 A2    12/1998

(Continued)

*Primary Examiner*—Hoa Q. Pham
(74) *Attorney, Agent, or Firm*—Stallman & Pollock LLP (57) ABSTRACT

This invention is an apparatus for imaging metrology, which in particular embodiments may be integrated with a processor station such that a metrology station is apart from but coupled to a process station. The metrology station is provided with a first imaging camera with a first field of view containing the measurement region. Alternate embodiments include a second imaging camera with a second field of view. Preferred embodiments comprise a broadband ultraviolet light source, although other embodiments may have a visible or near infrared light source of broad or narrow optical bandwidth. Embodiments including a broad bandwidth source typically include a spectrograph, or an imaging spectrograph. Particular embodiments may include curved, reflective optics or a measurement region wetted by a liquid. In a typical embodiment, the metrology station and the measurement region are configured to have 4 degrees of freedom of movement relative to each other.

16 Claims, 9 Drawing Sheets

U.S. PATENT DOCUMENTS

| | | | |
|---|---|---|---|
| 4,659,220 A | 4/1987 | Bronte et al. | 356/237 |
| 4,869,593 A | 9/1989 | Biegen | 356/351 |
| 4,899,055 A | 2/1990 | Adams | 250/372 |
| 5,042,949 A | 8/1991 | Greenberg et al. | 356/345 |
| 5,191,393 A | 3/1993 | Hignette et al. | 356/636 |
| 5,258,823 A | 11/1993 | Akamatsu | 356/615 |
| 5,291,269 A | 3/1994 | Ledger | 356/355 |
| 5,486,701 A | 1/1996 | Norton et al. | 250/372 |
| 5,517,032 A | 5/1996 | Imani | 250/372 |
| 5,563,709 A * | 10/1996 | Poultney | 356/613 |
| 5,604,344 A | 2/1997 | Finarov | 250/201.3 |
| 5,616,063 A | 4/1997 | Okumura et al. | 451/1 |
| 5,695,601 A | 12/1997 | Kodera et al. | 156/636.1 |
| 5,747,813 A | 5/1998 | Norton et al. | 250/372 |
| 5,757,502 A | 5/1998 | Weling | 356/376 |
| 5,825,498 A | 10/1998 | Thakur et al. | 356/394 |
| 5,835,225 A | 11/1998 | Thakur | 356/381 |
| 5,872,633 A | 2/1999 | Holzapfel et al. | 356/630 |
| 5,909,276 A * | 6/1999 | Kinney et al. | 356/237.2 |
| 5,943,122 A | 8/1999 | Holmes | 356/73 |
| 5,948,203 A | 9/1999 | Wang | 156/345 |
| 5,957,749 A | 9/1999 | Finarov | 451/6 |
| 6,052,188 A | 4/2000 | Fluckiger et al. | 356/369 |
| 6,108,091 A | 8/2000 | Pecen et al. | 356/381 |
| 6,108,092 A | 8/2000 | Sandhu | 356/381 |
| 6,111,634 A | 8/2000 | Pecen et al. | 356/72 |
| 6,120,348 A | 9/2000 | Fujita et al. | 451/5 |
| 6,142,855 A | 11/2000 | Nyui et al. | 451/67 |
| 6,157,450 A | 12/2000 | Marchese-Ragona et al. | 356/376 |
| 6,184,984 B1 | 2/2001 | Lee et al. | 356/369 |
| 6,406,641 B1 | 6/2002 | Galzarian | 216/85 |
| 6,413,867 B1 | 7/2002 | Sarfaty et al. | 438/689 |
| 6,690,473 B1 * | 2/2004 | Stanke et al. | 356/601 |

FOREIGN PATENT DOCUMENTS

| | | |
|---|---|---|
| GB | 2 314 037 A | 12/1997 |
| WO | WO 98/37404 | 8/1998 |
| WO | WO 99/01797 | 1/1999 |

* cited by examiner

APPARATUS FOR IMAGING METROLOGY

CROSS REFERENCE TO RELATED APPLICATIONS

This application is a continuation of U.S. Utility application Ser. No. 09/533,613, filed Mar. 22, 2000 now U.S. Pat. No. 7,042,580, which claims the benefit of priority to U.S. Provisional Application Ser. No. 60/118,217, filed Feb. 1, 1999, and U.S. Provisional Application Ser. No. 60/125,462, filed Mar. 22, 1999, and U.S. Utility application Ser. No. 09/495,821, filed Feb. 1, 2000, now issued U.S. Utility Pat. No. 6,690,473, all of which are incorporated herein in their entirety by reference.

BACKGROUND OF THE INVENTION

1. Field of the Invention

This invention relates to the field of optical metrology in general, and to in-line thin-film reflectometry and profilometry for semiconductor wafers in particular.

2. Description of Related Art

A trend towards smaller critical dimension sizes in integrated circuits (IC) drives advances in technology for semiconductor capital equipment. Both technical factors, such as the ratio of the critical dimension size to the wavelengths of light used by fabrication device components, and well known economic factors, such as wafer throughput, Cost-Of-Ownership (COO) and Overall Equipment Effectiveness (OEE) are critical.

In IC fabrication, hundreds of process steps are necessary. During some of these steps, successive layers of materials are deposited on a substrate. Subsequently, Chemical Mechanical Polishing (CMP) is often used to make a film layer planar to high degree of precision. After a CMP process step, the thickness of the remaining film may be determined to verify that it is within desired tolerances.

Optical methods are commonly used to determine the thickness of thin films since light is generally non-destructive and non-invasive. Measured optical properties of the surface or measured wave-optics effects due to the interaction of light with thin films residing on the wafer yield desired information, such as film thickness. Thus, as critical dimensions on the wafer are reduced, there is a need for advances in optical metrology to obtain required precision and accuracy.

Technical requirements of precision and accuracy must be consonant with economic requirements. Fabrication machines must process wafers at a rapid rate with high uniformity and high reliability in addition to high precision. Since the fabrication must take place in a strictly controlled environment, the size of the machine is also an important factor. Easy operation is also important, despite the complexity of the processing and measurements. Performance in terms of these and other economic factors can be expressed through figures-of-merit such as COO and OEE Wafer metrology art comprises mostly "metrology mainframe" devices, which are devices only partially integrated with an IC fabrication line. There are at least two significant problems associated with partially integrated or non-integrated metrology control. First, waiting for test measurements from metrology mainframe systems to confirm the results from each process step is inherently inefficient. Second, with a partially integrated or non-integrated unit, process engineers face difficulties in achieving and maintaining optimal process parameters once they have the measurement information.

These and other problems associated with off-line metrology result in growing need for integrated (in-line) metrology in IC wafer fabrication. With in-line devices, the metrology apparatus is physically placed within the process equipment itself. This enables a substantial reduction in times required to perform metrology measurements and shortens feedback or feedforward times between the metrology system and the process controls. By measuring critical parameters as each wafer is processed, the process equipment has information on the most recently processed wafer without stopping production. This results in good wafer-to-wafer control. Integrated metrology also significantly reduces operating costs by reducing the requirement for expensive test wafers, speeding up process qualifications and maintenance schedules, and provides an overall reduction in scrap wafers.

Related art in integrated thin-film metrology is limited regarding combining precise and accurate thin-film thickness measurements while meeting the other requirements of the semiconductor industry. Typically, related art in-line devices are limited to measurements of films of about 80 nm thickness. However, there is a need in the industry to measure film thickness of only a few tens of nanometers. Further, related art in-line devices are limited in their ability to make rapid, successive measurements over the totality of a wafer's surface.

What is needed is an imaging metrology system with rapid optical access to the entirety of a wafer surface. From the foregoing, it can be readily appreciated that many processes used in microelectronics manufacturing could benefit from integrated metrology, including but not limited to CMP, plasma etching, chemical vapor deposition, and lithography.

SUMMARY OF INVENTION

This invention is an apparatus for imaging metrology. One object is to integrate an imaging metrology station with a processor station such that the metrology station is apart from but coupled to the process station.

In one embodiment, a metrology device is provided with a first imaging camera with a first field of view containing the measurement region. Alternate embodiments include a second imaging camera with a second field of view. Preferred embodiments comprise a broadband ultraviolet light source, although other embodiments may have a visible or near infrared light source of broad or narrow optical bandwidth. Embodiments including a broad bandwidth source typically include a spectrograph, or an imaging spectrograph. Particular embodiments may include curved, reflective optics or a measurement region wetted by a liquid. In a typical embodiment, the metrology station and the measurement region are configured to have 4 degrees of freedom of movement relative to each other.

DETAILED DESCRIPTION

Figure 1:
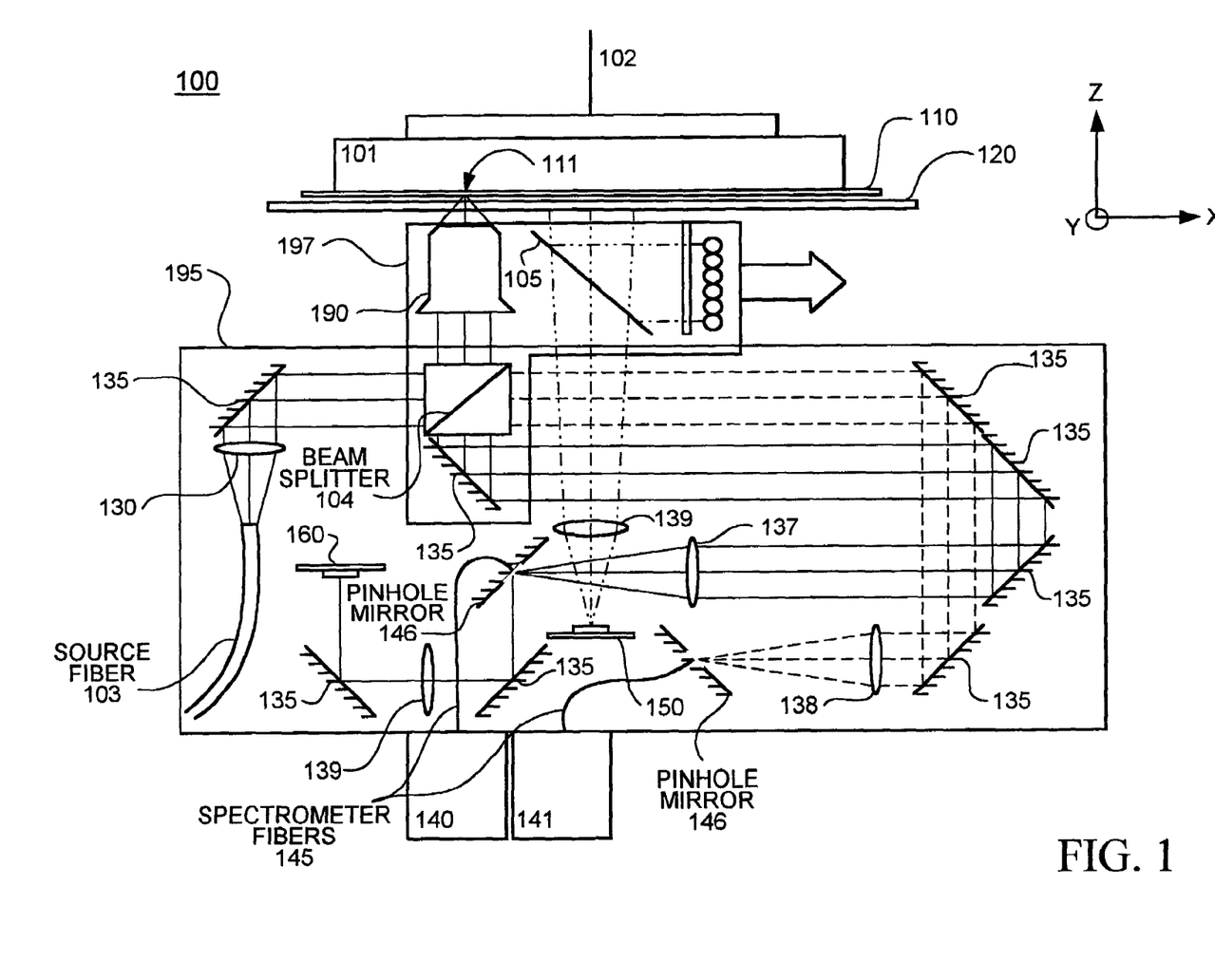
FIG. 1 shows a hardware overview for one embodiment of the wafer metrology device.

FIG. 1 illustrates one embodiment of an imaging metrology device. In FIG. 1, reflectometer assembly 100, vacuum chuck 101, vacuum chuck symmetry axis 102, light source fiber 103, first beam splitter 104, second beam splitter 105, semiconductor wafer 110, measurement region 111, window 120, collimator 130, relay optics 135, first imaging optical assembly 137, second imaging optical assembly 138, third imaging optical assembly 139, spectrographs (including calibration filters) 140 and 141, spectrograph fiber optic 145, pinhole mirrors 146, large field-of-view camera 150, small field-of-view camera 160, auto-focussing objective lens assembly 190, first optics breadboard 195, and second optics breadboard 197 are shown. The embodiment shown in FIG. 1 may be integrated as a subsystem into a process device (not shown) or in other embodiments may be a stand-alone mainframe. Other embodiments may include other diagnostic assemblies without departing from the invention, as described below.

In FIG. 1, semiconductor wafer 110 is coupled to vacuum chuck 101, whose center-of-mass is fixed relative to the laboratory and the semiconductor wafer coupled to it. However, rotation of the vacuum chuck about the vacuum chuck symmetry axis 102 is allowed. Reflectometer assembly 100 comprises window 120 and first and second optics breadboards 195 and 197, respectively. First optics breadboard 195 is free to translate along the y axis, and may be driven by a direct-drive actuator in a particular embodiment. Second optics breadboard 197 is coupled to the first optics breadboard, however, the second optics breadboard is free to translate relative to the first optics breadboard along the x axis. Objective lens assembly 190 is attached to the second optics breadboard, however, it is free to translate along the z axis as controlled by an auto-focus system known to the art. Thus, the embodiment shown in FIG. 1 has four degrees of freedom of movement: translation along the (x, y, z) axes; and rotation of the vacuum chuck about the vacuum chuck symmetry axis. This allows rapid optical access to the entirety of the wafer surface.

In the embodiment shown in FIG. 1, all optical elements except those on second optics breadboard 197 are coupled to and fixed relative to first optics breadboard 195. Objective lens assembly 190, are coupled to second optics breadboard 197. Thus, the objective lens assembly is free to translate along the x axis. In addition, the objective lens assembly may be focussed on semiconductor wafer 110 by translation along the z axis. Note that translations of the first and second optics breadboards along the x axis and y axis allow access to the full wafer surface. Rotation of the wafer coupled to the vacuum chuck may be used in combination with translations of the first and second optics breadboards along the x and y axes to allow more rapid measurement access over the entire surface of the semiconductor wafer or to eliminate obstructions. Complete coverage of a 200 mm diameter wafer is possible with straightforward scaling to 300 mm and larger diameter wafers.

In FIG. 1, vacuum chuck 101 not only holds wafer 110 but also flattens it. This enables more accurate auto-focus, and reduces measurement errors and uncertainties due to wafer tilt and associated variations in optical path length.

In the embodiment of FIG. 1 and in alternate embodiments, optics breadboards 195, 197 may be positioned with a direct drive motor/lead screw. In a preferred embodiment, components of a motor are mounted directly on a lead screw shaft according to well-understood mechanical techniques. With a direct drive motor/lead screw, coupling elements are eliminated resulting in a more compact drive mechanism with high stiffness in torsion that enables precision positioning of the breadboards relative to wafer 110.

The wavelength range for illumination and collection may be in the ultraviolet (UV) or the visible or the near infrared (NIR) in different embodiments. In the particular embodiment in FIG. 1, reflectometer assembly 100 comprises a broadband (UV, visible, NIR) reflectometer measurement system. Other embodiments may be narrowband or may comprise instruments other than a reflectometer. In FIG. 1, an illuminating light source (not shown) may be a UV Xenon lamp, fiber-coupled to the system shown in FIG. 1 via source fiber 103. Alternate embodiments have a tungsten lamp or a deuterium lamp or a xenon lamp. Relay optics 135 transfer collimated light from lens assembly 130 to beam splitter 104. The light transmitted directly through the beam splitter from the source fiber is referred to as the monitor beam. The monitor beam does not interact with measurement region 111. The portion of the illumination that the beam splitter directs toward the wafer is referred to as the measurement beam. The measurement beam reflects from the surface of the wafer, where its spectrum is modified by the presence of thin films on the wafer.

Following reflection from the wafer, the measurement beam returns to the beam splitter, and passes to several relay mirrors 135. First imaging optical assembly 137 focuses the measurement beam onto pinhole mirror 146. The light falling on a pin hole aperture in the pin-hole mirror passes into spectrograph fiber 145, which conveys it to spectrograph 140. The resulting spectrum is a primary source of information about the films on the wafer. Other embodiments may image a portion of the wafer surface onto a spectrograph slit, thereby collecting data along a line on the wafer surface rather than a point.

Referring again to FIG. 1, the monitor beam follows a similar but distinct path through another pinhole mirror 146 and spectrograph fiber 145 to spectrograph 141. The measured monitor spectrum is indicative of the illumination and optical components, and may be used to correct the measurement of film properties for instrument characteristics.

As described above, the relative spectral content of both the incident and reflected light from semiconductor wafer 110 is measured. The thickness of thin-films deposited on the measurement region 110 can then be determined from the reflected measurement beam and incident monitor beam light by principles well known in the art. Many data reduction methods are applicable.

The embodiment illustrated in FIG. 1 has several advantages. First, as described above, an entire wafer surface can be quickly accessed. In addition, scanning with relay mirrors is employed in only one spatial dimension. If the light beams reflected from the relay mirrors were perfectly collimated and aligned, scanning would have no deleterious effects on the performance of the system. However, the beams cannot be perfectly collimated and perfect alignment is unattainable in practice. Therefore, it would be preferable to scan the objective with respect to the rest of the optics as little as possible. In the embodiment shown in FIG. 1, the majority of the optics scan in one dimension on the first optics breadboard, and the rest of the optics scan in two dimensions with respect to a laboratory-fixed coordinate system, but only one dimension (X) with respect to the first optics breadboard. Thus, the relay scan length is no more than one wafer diameter. In related art devices, the optics are fixed, and the objective scans in two dimensions, requiring a scan length of up to two wafer diameters.

A further advantage of the embodiments shown in FIG. 1 is that the optical path length remains constant, regardless of scan position. Thus, if the object is treated as a focal point, with a specular reflection from the surface of the wafer, the amount of beam spreading does not change. In related art devices, spatial scanning over a wafer surface changes the total optical path length, and thus the amount of beam spreading suffered by a collimated beam.

According to an aspect of this invention, locating a particular region of a wafer for measurement is achieved by imaging at least one field-of-view of a surface of the wafer. In the embodiment shown in FIG. 1, reflectometer assembly 100 measures selected regions of semiconductor wafer 110 as located and identified by imaging cameras. Large field-of-view camera 150 and small field-of-view camera 160 image the wafer surface with an approximately 20 mm×27 mm and an approximately 1 mm×1.3 mm field-of-view, respectively. In FIG. 1, a portion of the measurement beam reflected by pinhole mirror 146 is refocused onto small field-of-view (SFOV) camera 160. The resulting image is indicative of patterns on semiconductor wafer 110. The pinhole itself is also imaged onto the SFOV as a dark spot superimposed on the image of the wafer's patterns. This dark spot indicates the precise location where the reflectometer measurement is made with respect to the patterns on the wafer. Alternate embodiments may include a Fresnel lens and a beamsplitter plate or utilize dark-field illumination.

Figure 7:
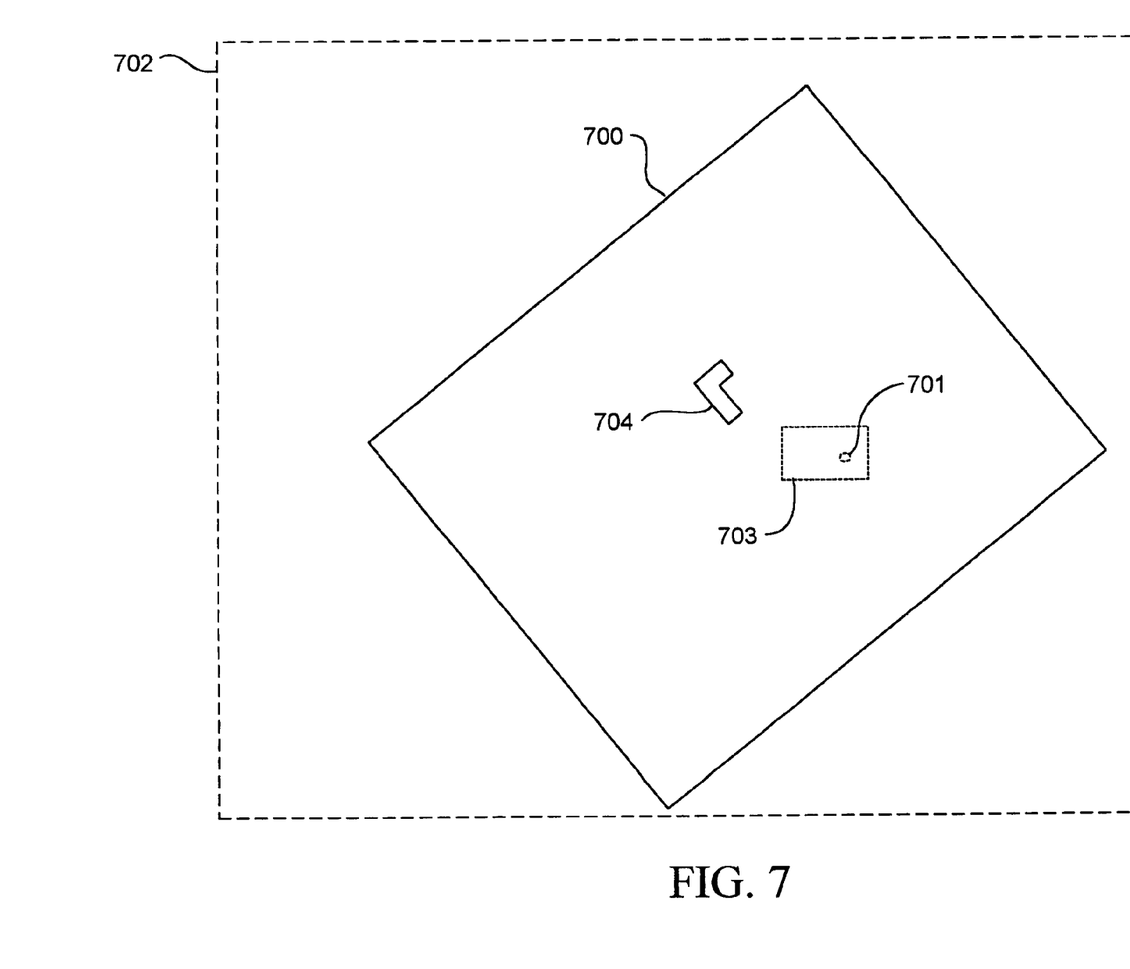
FIG. 7 illustrates the use of a large Field-Of-View (LFOV) camera and a small Field-Of-View (SFOV) camera to avoid groping in the process of locating a particular region of a wafer.

FIG. 7 illustrates the use of a large Field-Of-View (LFOV) camera and a small Field-Of-View (SFOV) camera to image a wafer surface and avoid groping in the process of locating a particular region of a wafer. In FIG. 7, die 700, LFOV 702, SFOV 703, LFOV pattern 704, and SFOV pattern 701 are shown.

LFOV 702 is generally larger than die 700, and much larger than the uncertainty in the location of the center of the wafer. Thus, it can be moved to a location where it will certainly find LFOV pattern 704 on a die of a randomly oriented wafer. Once the LFOV pattern has been found, the system has much better knowledge of both the orientation of the wafer and the location of its center. Thus it is able to position the SFOV 703 over the SFOV pattern 701 without groping. This process has a deterministic time that is much shorter than the worst-case scenario for groping with just a SFOV, or than the time for physically aligning the wafer.

Figure 8:
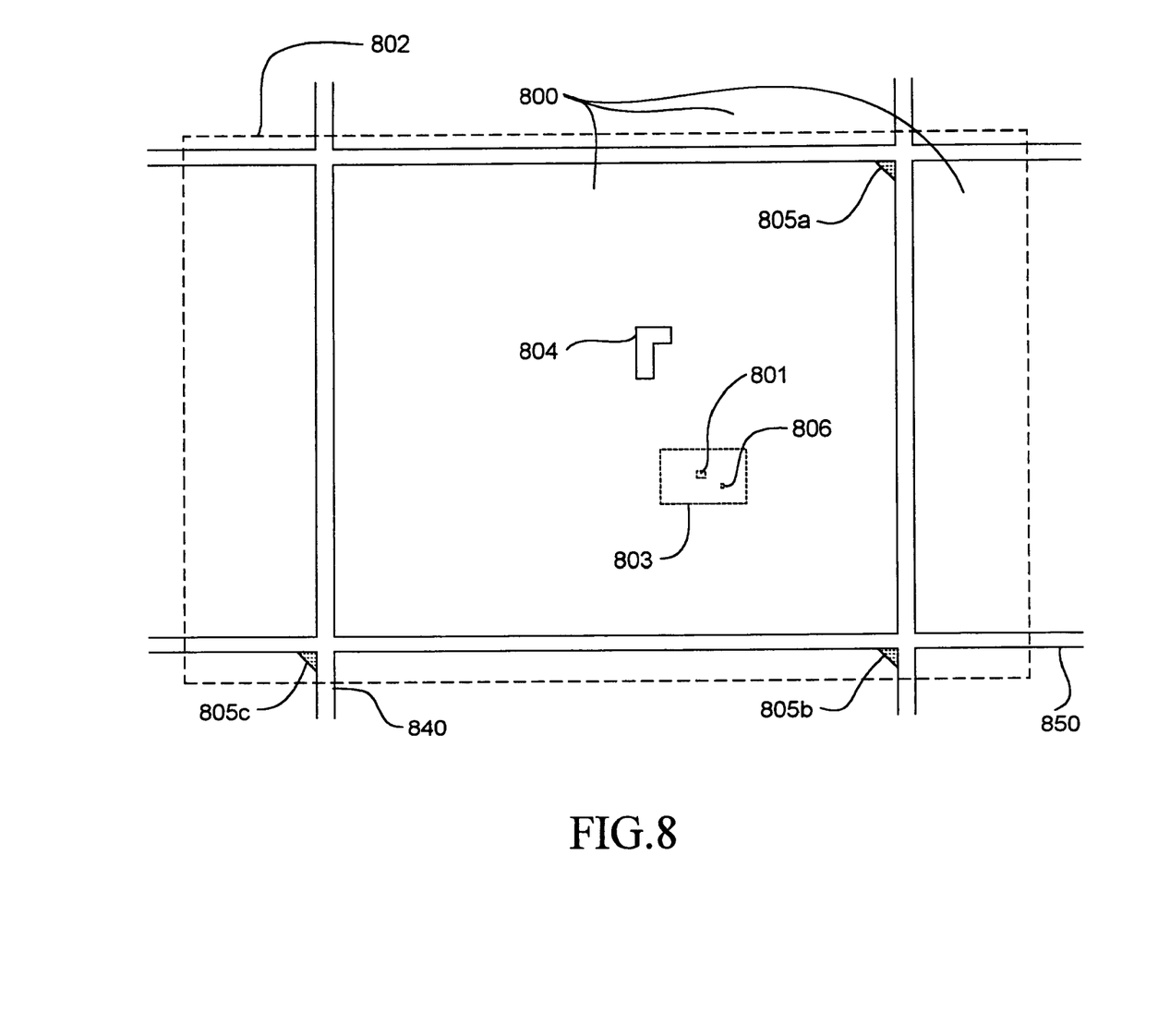
FIG. 8 illustrates the advantage of using of the LFOV camera to enable easy die size determination during training.

FIG. 8 illustrates the advantage of using of the LFOV camera to enable easy die size determination during training. In FIG. 8, dies 800, inter-die streets 840, inter-die alleys 850, die features 805a–c, large field of view 802, small field of view patterns 803, 804 and 801, and measurement site 806 are shown.

For training purposes, operators find it advantageous to view the wafer right side up, and moreover to orient the wafer so that inter-die streets 840 and alleys 850 appear vertical and horizontal, as shown in FIG. 8. However, such an orientation of the wafer is not necessary and other orientations are possible in alternative embodiments. An initial rough estimate of die size can be made from three occurrences of a die feature, eg. 805a–c, selected by the operator on three different dies. The system can then use pattern recognition and the LFOV and/or SFOV cameras to obtain a very accurate determination of die size by locating LFOV and/or SFOV patterns, 804 and/or 801, on various dies on the wafer. With this method, it is not necessary for the operator to know the die size a priori.

Another advantage of the LFOV camera is ease of training human operators to correlate measurement sites and patterns in the SFOV with the position on the wafer. Ideally, the large field of view covers a whole die, as shown in FIG. 8. Using large field-of-view 802, an operator can select the region of the die 800 to view with SFOV 103. This is similar to using a state map to navigate to a particular city. Once the SFOV has been properly positioned, the operator can very precisely select SFOV pattern 801 and the measurement site 806. This is similar to finding the correct intersection on a city map.

In a preferred embodiment, there may be a multiplicity of measurement sites within a die. In such cases, different sites may have different 'stacks' of layers that are to be measured. The thickness algorithm, i.e., the parametric minimization of a cost function as discussed in U.S. Provisional Application Ser. No. 60/125,462, generally needs to have a priori information, the algorithm recipe, about each stack that is measured. In cases where there are multiple sites per die with different stacks, the system must either use multiple algorithm recipes, or have a general algorithm recipe to accommodate the different stacks.

The reflectometer shown in FIG. 1 is included for purposes of illustration and not limitation. Alternate embodiments of the imaging metrology device comprise other metrology systems, including acoustic systems. Such alternate metrology system may be coupled to the same optics breadboards shown in FIG. 1 for reflectometer system 100. Particular embodiments may also require the use of flexural bearings for smooth repeatable motion on micrometer or sub-micrometer scales.

Exemplary alternative embodiments include a profilometer to determine amounts of recess, dishing, or other departures from planarity of a wafer surface and a profilometer in combination with a reflectometer. In different embodiments, a profilometer may be an acoustic profilometer or an optical profilometer. A particular embodiment of an optical profilometer may use the auto-focus system described in U.S. Provisional Application Ser. No. 60/125,462, to determine a relative profile of a wafer surface. The auto-focus system is inherently sensitive to the profile of the wafer surface since departures from planarity of the wafer surface will cause differences in the focussing of light rays reflected from the wafer surface.

Other embodiments of this wafer metrology device may include an ellipsometer or high-contrast imaging microscopes. Particular embodiments may utilize aspects of differential interference contrast (DIC) techniques. Polarization techniques may be incorporated to infer quantitative information about the wafer surface according to techniques well known in the art. In particular embodiments, an integrated interferometer, and imaging spectrograph may be used to simultaneously determine the wafer surface's profile and material content. Preferred embodiments further comprise motion control systems, image pattern recognition systems, and software to determine the quantities of interest from measured data. These elements are well-known in the art.

It is noteworthy that in the embodiment shown in FIG. 1, semiconductor wafer 110 is located above reflectometer assembly 100. In alternative embodiments, the semiconductor wafer may be held in a pool of water above or below the optical system. With the wafer below the optics, the system may be configured to 'look' down instead of up. This would necessitate differences from FIG. 1 in the handling of the wafer, which would have its IC device side up. In such alternate embodiments, either the optical system (including a main window) may be lowered toward the semiconductor wafer or the semiconductor wafer may be raised toward the optical system. Such an alternate embodiment would be a 180 degrees rotation of the system about a horizontal axis, as compared to FIG. 1. General rotations of the system relative to the configuration shown in FIG. 1 are also possible, e.g., 90 degrees. The main impact of such rotations is on the wafer handling techniques.

In particular alternative embodiments of the invention, there may be no water in the measurement path. That is, the instrument is 'dry'. In such embodiments, the orientation of the instrument relative to the laboratory may be arbitrary. For example, the embodiment of FIG. 1 could be operated on its side or upside down. While redesign of some of optical components might be preferred in such cases, it would not be necessary.

As can be appreciated by the skilled person, many other optical layouts than that shown in FIG. 1 are also possible without departing from the invention, including embodiments using substantially all reflective optics including curved reflectors. As one skilled in the art will recognize, the use of reflective optics has several advantages including minimizing Fresnel reflections, and chromatic bandwidth limitation and aberrations. In certain embodiments, however, refractive optical components are preferred since reflective optics may introduce constraints on aperture and geometry. In such embodiments, the optical system is color-corrected and if the semiconductor wafer is immersed in water, the water is considered as an optical component.

Figure 2:
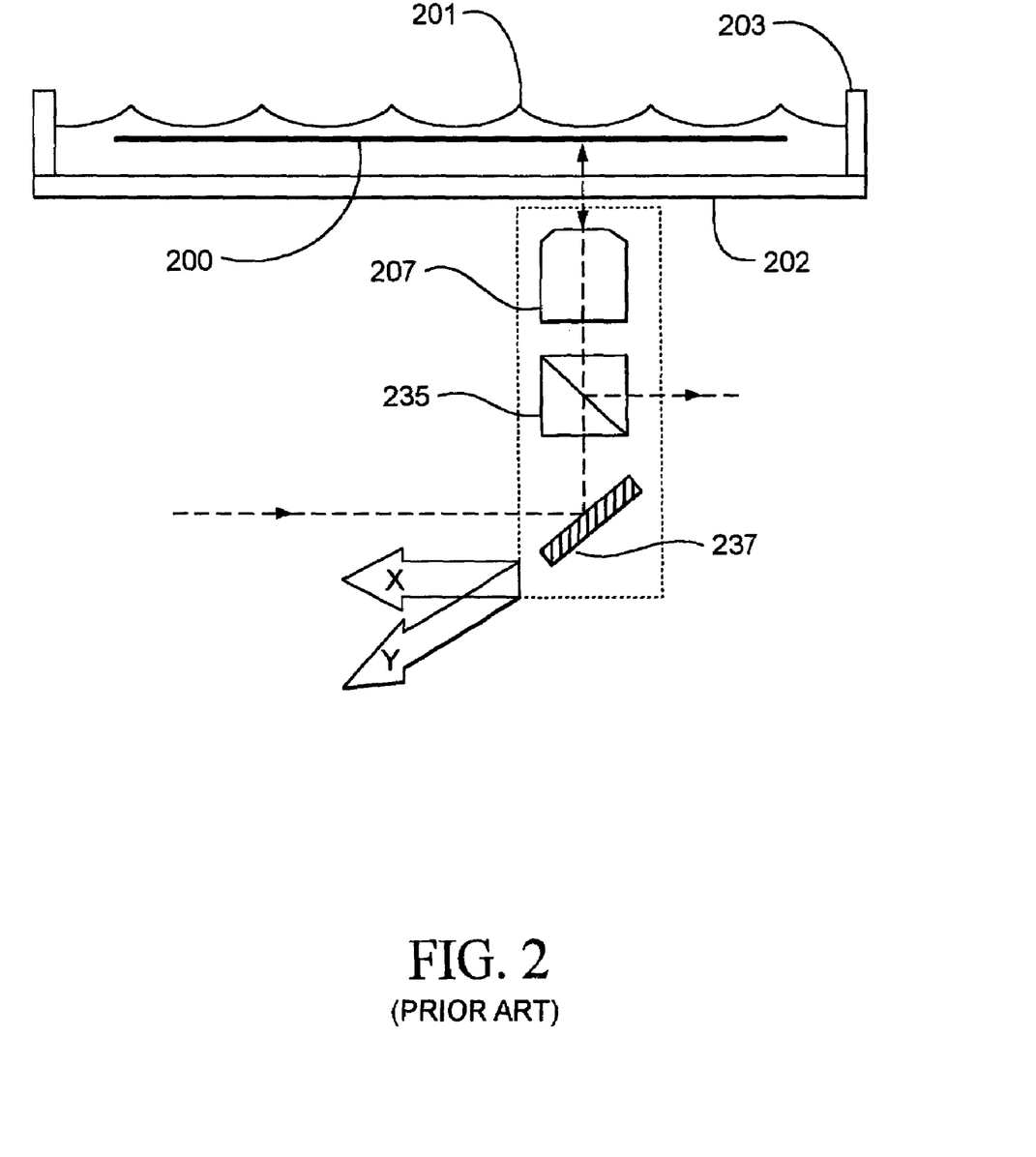
FIG. 2 illustrates a prior art device with a single large window.

FIG. 2 illustrates a prior art device with a single large window fixed relative to the laboratory. In FIG. 2, wafer 200, water surface 201, containment wall 203, objective lens assembly 207, beam splitter 235, relay optic 237, and window 202 are shown. It is noteworthy that this prior art device utilizes a single large window 202. For accurate measurements, window 202 must be of optical quality. Due to the size of the window, this can lead to considerable expense.

Figure 3:
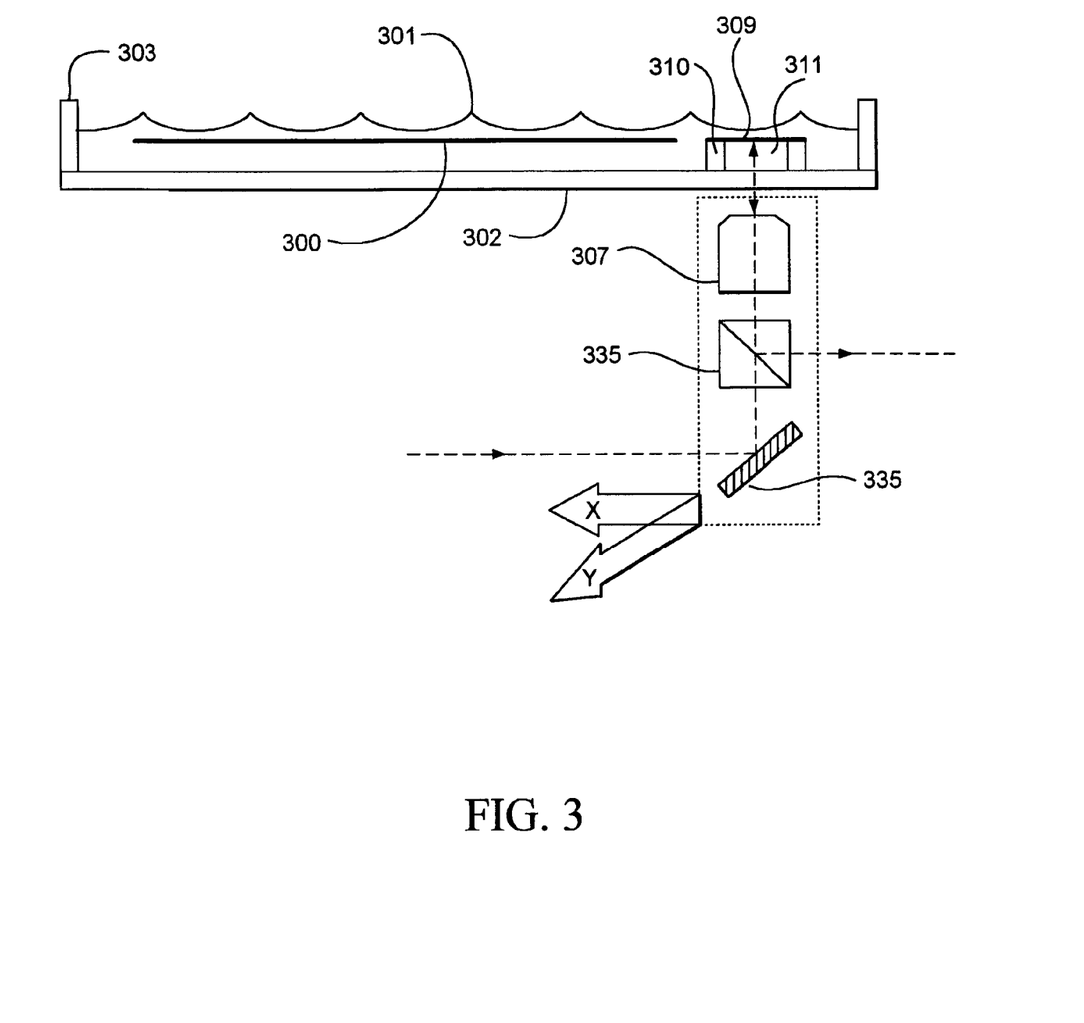
FIG. 3 shows an exemplary reference reflector embodiment.

To achieve accurate measurement results when a data reduction method, preferred embodiments use a reference reflector to collect data allowing a correction for slowly varying characteristics of the measurement system in a data reduction method. FIG. 3 shows an exemplary embodiment with a reference reflector. In FIG. 3, wafer 300, window 302, reference reflector 309, reference volume walls 310, reference volume 311, main volume of water 301, objective lens assembly 307 and relay optics 335 are shown.

In FIG. 3, reference volume walls 310 separate the reference volume 311 from the main volume of water 301. Reference volume 311 may be filled with air, water, or other suitable substances. It is preferred that the reflectivity of reference reflector 309 is very stable over time. The distance between window 302 and the reference reflector can be adjusted if volume 311 is not filled with water, to put the reflector in focus when the objective lens assembly 307 is the same distance below the window 302, as when the wafer is in focus. In a preferred embodiment, the volume is filled with an inert solid, and the height of the reflective surface above the window 302 is adjusted appropriately.

Reference reflector 309 may be of silicon, fused silica, chromium or any other inert material. It may comprise layers of deposited material on a substrate to achieve mechanical and optical stability. In a preferred embodiment, the reference reflector comprises a fused silica substrate with a chromium film on a top surface. An alternative embodiment of the reference reflector uses silicon with a reflective oxide layer on a lower surface.

Referring to FIG. 3, reference reflector 309, reference volume walls 310 and the window 302 may be assembled in differing ways. In a preferred embodiment, the reflector and window are hermetically sealed to the window. In an alternative embodiment, the reference reflector, reference volume walls and the window are held together with a polymer adhesive, e.g., epoxy or super glue. In other embodiments, volume 309 is not sealed off from main volume 301. The components are either bonded together or held in place mechanically, for example with stops and springs. The reference volume is sealed in order to preserve the reflectance of the reflector, i.e., to avoid it getting dirty or corroded due to materials introduced into the bath, e.g., CMU slurry. Sealing volume 311 avoids the problem of breaks or leaks caused by different thermal expansion coefficients, either during operation or shipping.

In preferred embodiments, reference reflector 309 is placed in a position where the objective lens assembly 307 can have direct access to it. Preferably, the objective lens assembly can scan in at least one dimension, and move to the location of the reference reflector. However, in embodiments where the wafer scans over the objective, the reference reflector may do so as well. While a preferred embodiment has the wafer above the objective lens assembly as illustrated in FIG. 3, alternate embodiments may have the objective lens assembly above the wafer, or at an arbitrary inclination.

According to aspects of this wafer metrology device described above, a reference spectrum from the reference reflector 309 is collected periodically. Following collection of a reference spectrum a data reduction algorithm utilizing the reference spectrum is used to calculate film thickness from spectra collected from wafer 300. Preferably, a reference spectrum is collected every time just prior to a wafer measurement. There are numerous ways to include the reference spectrum from the reference reflector into a data-reduction algorithm. In one embodiment, every spectrum from the wafer is normalized with the most recently measured reference spectrum from the reference reflector.

Calibration of the measurement apparatus may utilize a calibration wafer and the spectrum collected from it. Calibration adjusts the algorithm described above so that it gives the correct answer for the calibration wafer. The reference spectrum should be used by the algorithm at calibration in the same way that it is used during measurements of wafers, so that any changes in the system between the last calibration and the current measurement will not affect the results of the algorithm.

As described, embodiments of this wafer metrology device (see FIG. 1 and FIG. 3) may include a reference reflector and dual spectrographs. The primary data for the measurement is the spectrum S, which is the system's output representing reflection from the sample under test. In addition to the properties of the sample, S depends on the characteristics of the broadband (UV, visible, NIR) illumination, the optical system, detectors and digitizers and other elements that comprise a measurement system. Such measurement system characteristics obscure information about the sample. Thus, an accurate measurement of film thickness should remove their effects.

Some characteristics of a measurement system change significantly with time, and others may be substantially constant. In a preferred embodiment of this invention, an arc lamp is the light source. Flickering of the arc in its housing produces very fast changes. Bending or flexing of source fiber 103 (see FIG. 1) and changing an optical path length due to scanning may give rise to fast changes. Aging of the lamp may produce slow changes.

According to aspects of this invention, dual spectrographs may collect two spectra essentially simultaneously, a reflection spectrum from the sample under test and the monitor spectrum that does not interact with the sample under test, as shown in FIG. 1.

In FIG. 1, a beam splitter divides the reflected beam from the monitor beam, which proceeds straight through the beam splitter to the spectrograph 141. The reflected beam proceeds from the beam splitter, through the objective and to the sample, back through the objective and beam splitter to a mirror which deflects it parallel to the monitor beam to spectrograph 140. It is understood that the paths from the beam splitter and mirror to the respective spectrometers may include other optical components which are not shown in FIG. 1 but are, in a preferred embodiment, as similar as possible for the two beams. In the case where the sample is the sample under test, e.g., a wafer that has just been polished, the reflection spectrum is the measurement spectrum S, and its associated monitor spectrum is $S_m$. The monitor spectrum is used to correct for rapid changes in the system, e.g., flickering of the illumination source.

In FIG. 1 the sample under test is the semiconductor wafer 110. It is noteworthy that the sample may also be the reference reflector or the calibration reflector, as discussed above. From FIG. 1, the optical path for light determining the monitor spectrum may be similar to the optical path for the light determining the measurement spectrum, except for transit to and from measurement region 111. A preferred embodiment of the two beams is shown in FIG. 1. In preferred embodiments, the illumination source may be identical for both beams.

Figure 4:
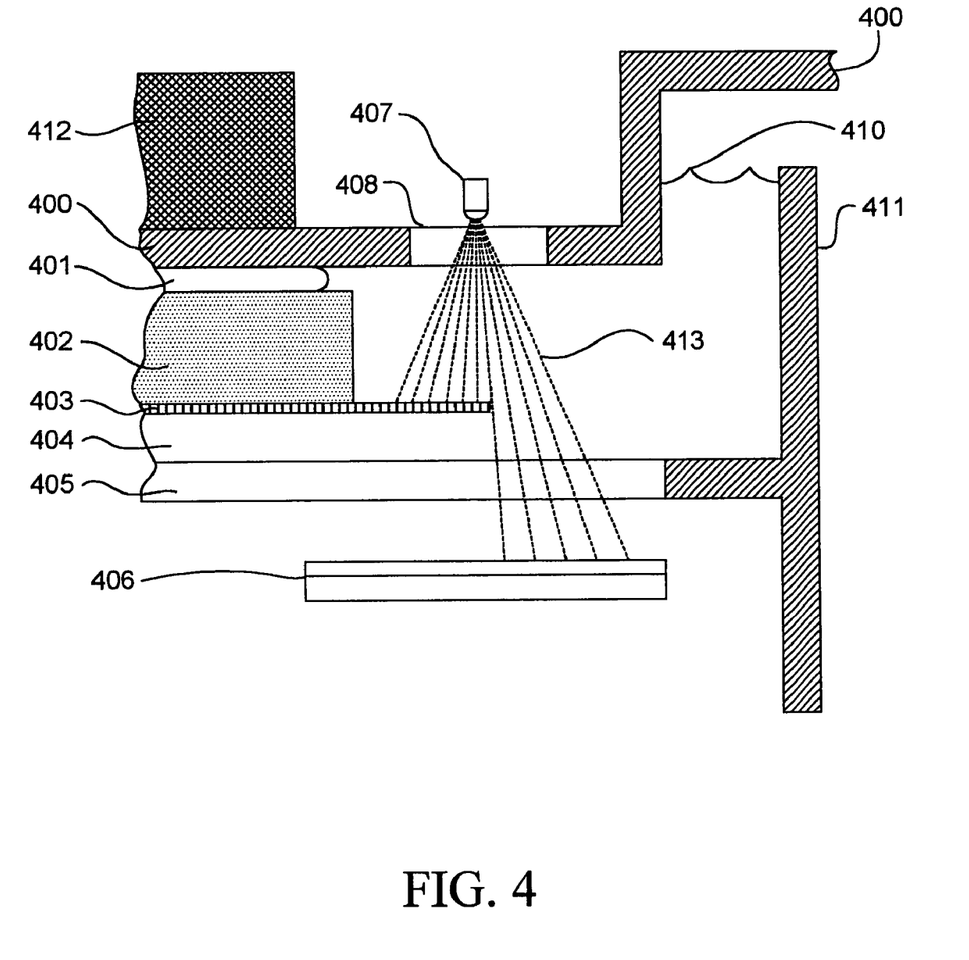
FIG. 4 shows an exemplary embodiment of the wafer aligner.

FIG. 4 shows an exemplary embodiment of the alignment system allowing rapid alignment of a wafer with the optical system. In FIG. 4, wafer 403, rotary chuck 402, motor 412, water 404, window 405, water level 410, motor housing 400, rotary seal 401, light source 407, light 413, alignment window 408, detector 406, and tank wall 411 are shown.

In FIG. 4, rigid rotary chuck 402 holds wafer 403. Motor 412 turns the rigid rotary chuck about an axis (not shown). Water 404 fills the area above main window 405 up to water level 410 and over to tank wall 411. Rotary seal 401 seals motor housing 400 from the water. Light source 407 is also in a dry housing. The light source produces light 413 that passes through alignment window 408 from the dry housing into the water. Detector 406 is in the dry volume below window 405. Some of the light 413 strikes wafer 403 and is blocked. The rest of the light passes through main window 405 into the dry volume below it, and onto the detector.

Rigid rotary chuck 402 rotates wafer 403. As the wafer rotates, the edge of the wafer that is directly over the detector moves in a radial direction (to the left and right in FIG. 4). The radial motion arises due to the wafer being off-center on the rigid rotary chuck or not being perfectly round. Aside from machining tolerances, the presence of a fiducial notch or flat on the rigid rotary chuck causes the wafer to be out of round.

Radial motion of the edge of wafer 403 over detector 406 changes the shadowing of light 413 which falls upon the detector. The detector can be either a single long detector, e.g., a photo-diode, or an array of detectors, e.g., a charge coupled device (CCD). In the former case, the total amount of the light falling on the detector is an indication of position of the edge of the wafer. As the edge of wafer 403 moves to the right in FIG. 4, the amount of light falling upon the detector decreases. In general, the output of the detector, I, is some function of the position of the edge of the wafer, $x_e$;

$$I=f(x_e), \quad (1)$$

The quantity I is not necessarily linear but is monotonic, so that its inverse $$x_e=f^{-1}(I), \quad (2)$$

may be used to determine the location of the edge.

In an alternate embodiment, the detector may consist of an array of detectors, with each element in the array having a different location, $x_a$. In this case the intensity of light falling on the different detector elements gives rise to a waveform:

$$I(x_a)=g(x_e). \quad (3)$$

The quantity I can be processed by an algorithm, h, such that $$x_e=h(I(x_a)) \quad (4)$$

Functions g and f may be complicated, due to wave-optics considerations (FIG. 4 is illustrative only of ray-optics). Determination of f or g is by calibration.

Figure 5:
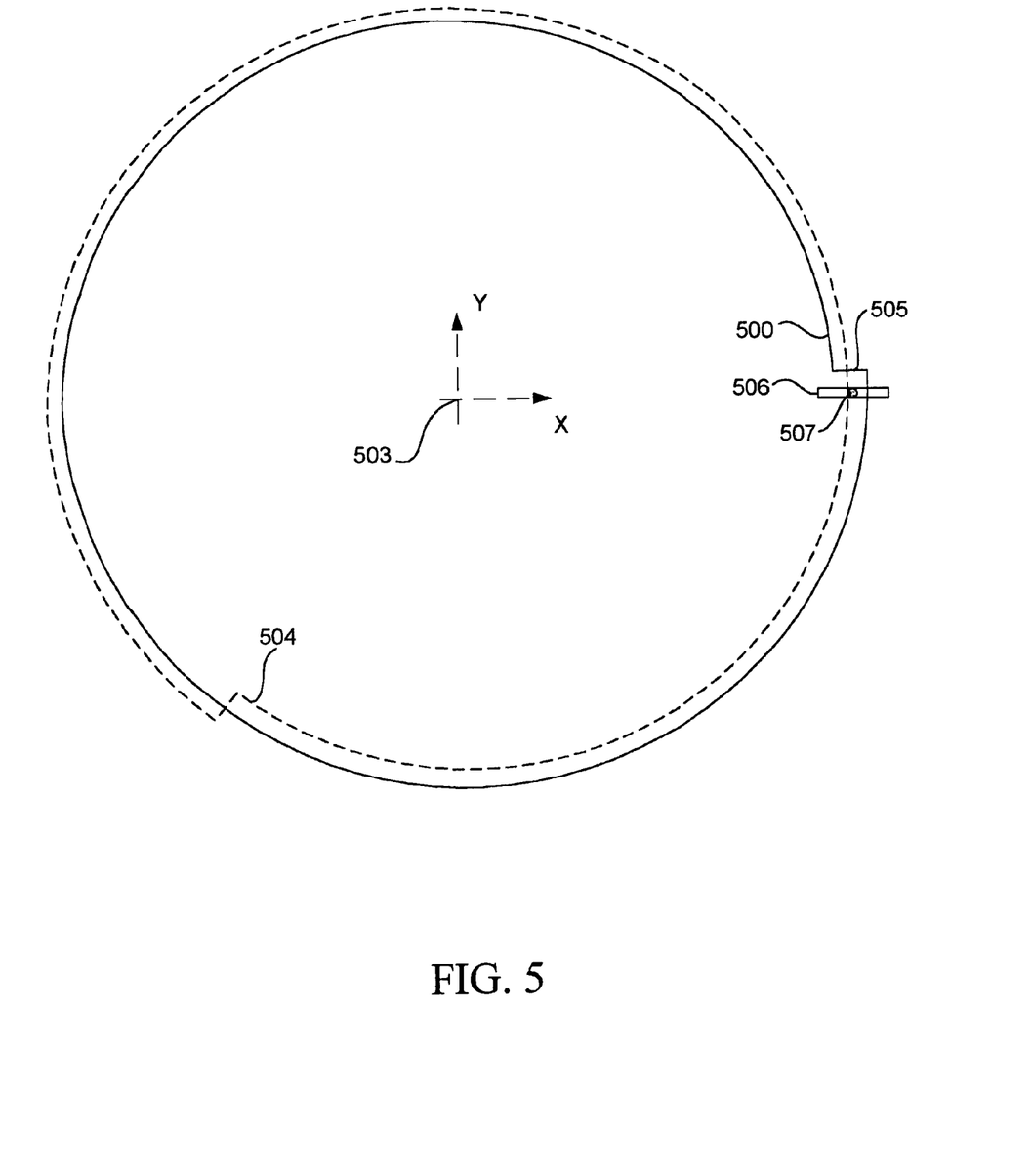
FIG. 5 illustrates calibration of the wafer aligner.

FIG. 5 illustrates calibration of the wafer alignment. In FIG. 5, spiral wafer 500, chuck 503, spiral edges 504 and 505, detector 506, and source 507 are shown.

Spiral wafer 500 has a thickness comparable to that of a silicon wafer; is made from a durable, clean, machinable, opaque material, eg, stainless steel; and has a mechanical index to insure that its center is aligned with the center of the chuck 503. As the chuck rotates, the spiral edges 504 and 505 block amounts of light emanating from source 507 from reaching detector 506. As the spiral rotates, the system records the detector output as a function of angle. The discontinuity in the radius of the spiral 505 indicates when the spiral is over the detector. The radius of the spiral as a function of angular displacement from the discontinuity 505 is known. Thus, the functions $g(x_e)$ or $f(x_e)$ can be recorded, so that $f^{-1}$ or h can be calculated for use with real wafers.

The outcome of the above-described measurement enables the calculation of the location of a notch or flat on the wafer, and the location of the center of the wafer with respect to the center of the chuck, from I for a set of rotations covering 360 degrees with $f^{-1}$ or h.

Figure 6:
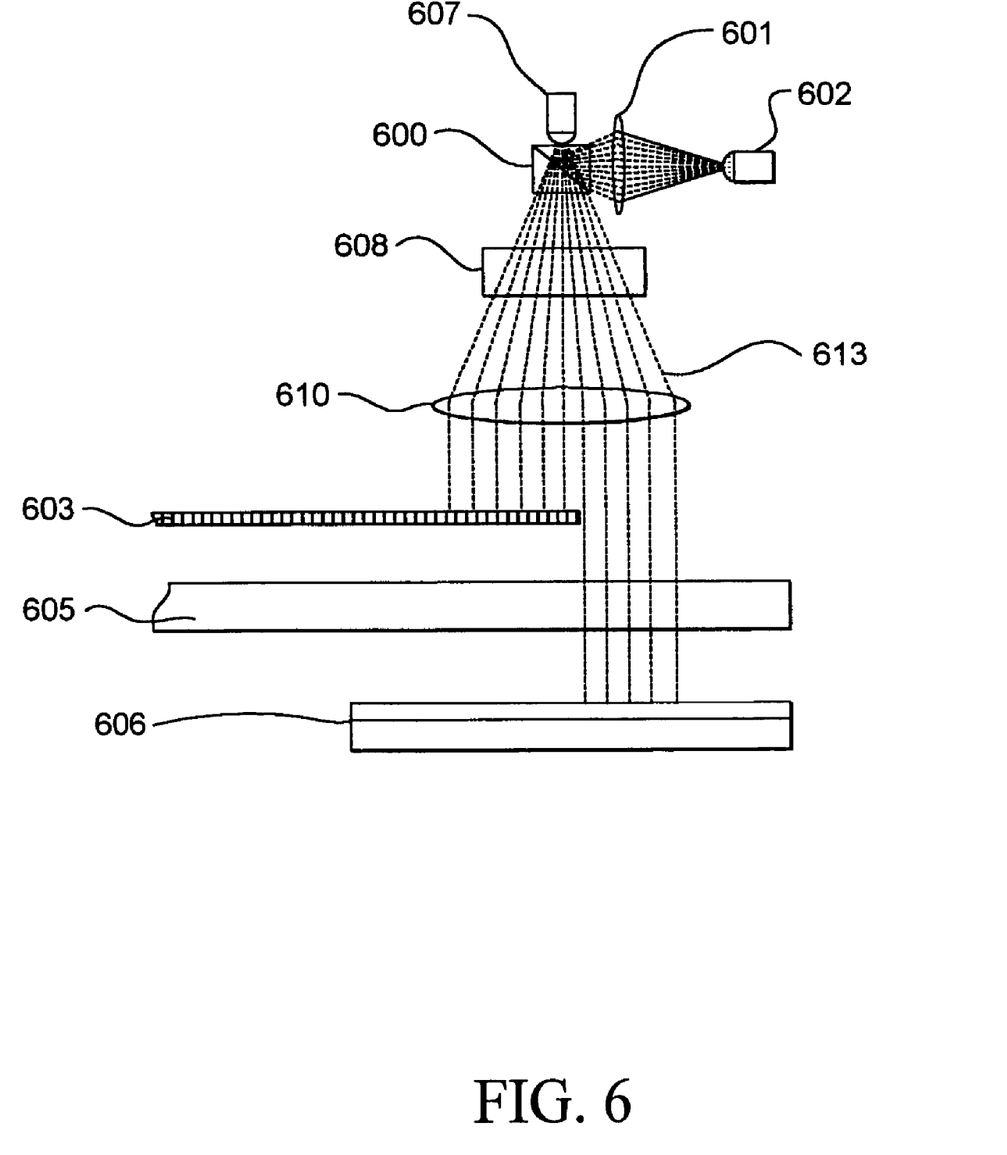
FIG. 6 illustrates improved accuracy of wafer alignment.

FIG. 6 shows another aspect of the wafer metrology device that improves the accuracy of wafer alignment. In FIG. 6, beam splitter 600, lens 601, reference detector 602, light source 607, window 608, rays 613, collimating lens 610, and wafer 606 are shown.

In general, the intensity of the source 607 can vary as a function of, eg, time and temperature. In order to correct or compensate for this, some portion of the light can be deflected by a beam splitter 600, possibly focused by lens 601, and detected by reference detector 602. The output from the reference detector can be used either to control the output intensity of the source, or to correct the inversion of data for variations in the source.

FIG. 6 shows another exemplary illumination scheme. In this case the source 607 produces diverging light. In this embodiment, lens 613 collimates the rays 613. In other embodiments a collimated source may be used. Additional embodiments may uses a diffusing element following the source in order to homogenize the spatial mode profile of the source.

There are three distinct advantages to wafer alignment: First, during training the operator can always view the wafer "right-side-up," e.g., with the notch in the direction towards the bottom of the view screen. This makes training of the system easier. Second, pattern recognition is more difficult with arbitrary orientations of the wafer. The better the initial alignment, the easier is pattern recognition. Third, the pinhole can have a square cross section (perpendicular to the measurement or monitor beams), which allows for greater light transmittance without an increase in the minimum box size that can be used for the measurement.

Embodiments of this wafer metrology device may be integrated into a wafer processor. As described above, different embodiments of this wafer metrology device allow it to be at different positions relative to the wafer under test. Particular embodiments utilize raiser and feeder elements to take wafers from other locations and introduce them to an apparatus according to this wafer metrology device.

Figure 9:
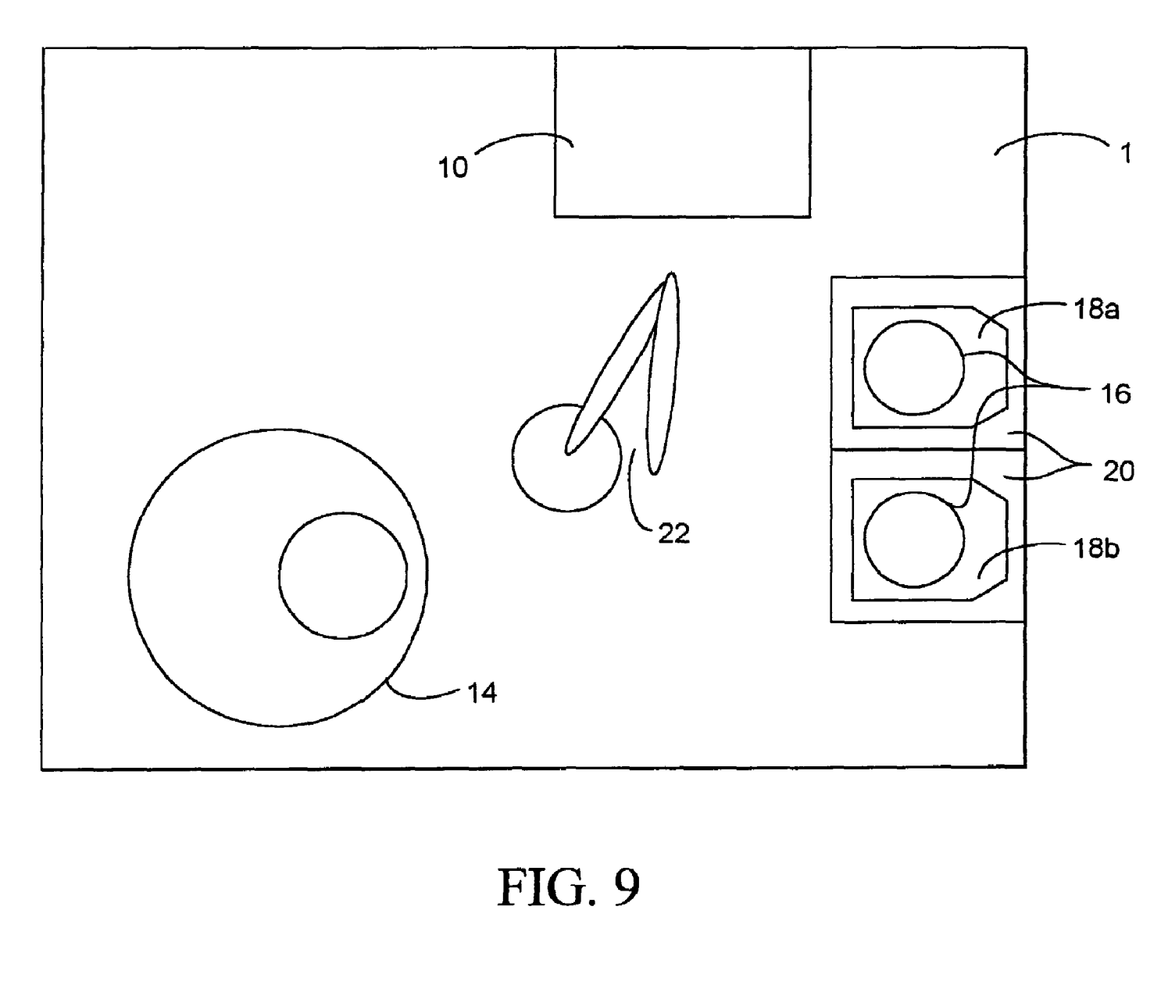
FIG. 9 illustrates one embodiment of an integrated metrology apparatus.

FIG. 9 shows a preferred embodiment integrated with a wafer process station in a fabrication line. For purposes of illustration and not limitation, the process station in the embodiment in FIG. 9 is a polisher. A polishing machine 1 and an integrated surface metrology station, ISMS 10, are shown. The polishing machine 1 comprises a polishing unit 14, loading areas 18 and transport system 22. In addition, wafers 16 in carriers 18 are shown. As shown in FIG. 9, the metrology station is apart from the process station and coupled to the process station.

Wafers 16 are brought to and taken from polishing machine 1 in carriers 18 through loading areas 20. The carriers may be cassettes or FOUPs, terms common in the art. Transport system 22 is a device or set of devices for transporting the wafers within polisher 1. Specific embodiments may comprise a robot, such as the Equipe WTM-105. The transport system can move the wafers to any of the carriers 18, the polishing unit 14 or the ISMS 10.

The foregoing description of various embodiments of the invention has been presented for purposes of illustration and description. It is not intended to limit the invention to the precise forms disclosed. Many modifications and equivalent arrangements will be apparent.

What is claimed is:

1. A method of fabricating a semiconductor wafer, the method comprising:
   (a) transferring a processed wafer from a wafer process station located within a process chamber to a metrology station also located within the process chamber, but spaced apart from the wafer process station, the metrology station containing a chuck for receiving and supporting the wafer and a measurement head for measuring the wafer, the wafer process station containing a transport system for supporting the wafer during processing by the wafer process station;
   (b) while the wafer is supported in the chuck of the metrology station
      (i) imaging a surface of the wafer with a camera in order to locate a selected measurement region of the surface containing at least one feature on the surface;
      (ii) directing a broadband light beam toward the measurement region;
      (iii) obtaining a first measurement of spectral content of the broadband light beam which has been reflected from the measurement region of the wafer;
      (iv) obtaining a second measurement of spectral content of the broadband light beam which has not been reflected from the wafer; and
      (v) receiving the first and second measurements at a processor and evaluating the wafer based on the first and second measurements, where the second measurement is used to correct for system characteristics.

2. A method as in claim 1, and wherein the step of directing the broadband light beam toward the wafer includes using a beam splitter positioned along a beam path of the broadband light beam.

3. A method as in claim 1, and wherein the step of directing the broadband light beam toward the wafer includes using a mirror positioned along a beam path of the broadband light beam.

4. A method as in claim 1, and further comprising:
   focusing the broadband light beam on the sample using an objective lens of the measurement head.

5. A method as in claim 1, and further comprising:
   loading the wafer into the wafer process station using a transport system.

6. A method as in claim 5, and further comprising:
   processing the wafer in the process station.

7. A method as in claim 1, and wherein the first and second measurements are obtained simultaneously.

8. A method as in claim 1, and wherein the broadband light beam is generated by a UV light source.

9. A method as in claim 1, and wherein the broadband light beam is generated by a light source defined by at least one lamp, said light source emitting a range of wavelengths, said range of wavelengths including visible and ultraviolet light.

10. A method as in claim 1, and wherein the broadband light beam is generated by a lamp selected from the group consisting of a UV xenon lamp, a tungsten lamp, a deuterium lamp and a xenon lamp.

11. A method as in claim 1, and further comprising:
   detecting an edge position of the wafer while the chuck is rotated in order to determine a position offset of the sample.

12. A method as in claim 1, and further comprising:
   passing the broadband light beam, reflected from the wafer, through a pinhole mirror before obtaining the first measurement.

13. A method as in claim 12, and further comprising:
   receiving a reflected portion of the broadband light beam, reflected by the pinhole mirror, to a camera for determining a measurement position relative to the wafer.

14. A method as in claim 13, and further comprising:
   focusing the pinhole of the pinhole mirror onto the camera in order to determine a precise measurement position relative to the wafer.

15. A method as in claim 1, and wherein the position of the objective lens relative to the wafer can be adjusted without altering an optical path length of the metrology station.

16. A method of fabricating a semiconductor wafer, the method comprising:
   processing a wafer in a process station located within a process chamber while the wafer is supported in the process station by a process station transport system;
   transferring the processed wafer from the process station to a chuck in a metrology station also located within the process chamber, but spaced apart from the process station, the chuck operable to accurately support the wafer in at least one position relative to a measurement head of the metrology station, the measurement head being operable to measure a parameter of the wafer;

imaging a surface of the wafer with a camera of the metrology station in order to locate a selected measurement region of the surface containing at least one feature on the surface;

directing a broadband light beam toward the measurement region;

obtaining a first measurement of spectral content of a portion of the broadband light beam which has been reflected from the measurement region of the wafer;

obtaining a second measurement of spectral content of the broadband light beam which has not been reflected from the wafer; and receiving the first and second measurements at a processor and evaluating the parameter of the wafer based on the first and second measurements, where the second measurement is used to correct for system characteristics.

* * * * *